(12) United States Patent
Kitano

(10) Patent No.: US 8,177,405 B2
(45) Date of Patent: May 15, 2012

(54) ILLUMINATION OPTICAL SYSTEM OF ENDOSCOPE

(75) Inventor: Ryou Kitano, Minato-ku (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 12/962,373

(22) Filed: Dec. 7, 2010

(65) Prior Publication Data

US 2011/0134656 A1    Jun. 9, 2011

(30) Foreign Application Priority Data

Dec. 8, 2009    (JP) .................................. 2009-278506

(51) Int. Cl.
*A61B 1/06* (2006.01)

(52) U.S. Cl. ........ 362/574; 362/326; 362/554; 362/558; 362/572

(58) Field of Classification Search ............. 362/311.01, 362/311.03, 311.05, 326, 554, 558, 572, 362/574; 600/182

See application file for complete search history.

(56) References Cited

U.S. PATENT DOCUMENTS

| | | | | |
|---|---|---|---|---|
| 4,153,356 | A * | 5/1979 | Hama | 396/17 |
| 7,585,274 | B2 | 9/2009 | Homma | |
| 2003/0103199 | A1 * | 6/2003 | Jung et al. | 356/73 |
| 2007/0270653 | A1 * | 11/2007 | Vayser et al. | 600/182 |

FOREIGN PATENT DOCUMENTS

| | | |
|---|---|---|
| JP | 61-177416 A | 8/1986 |
| JP | 5-119272 A | 5/1993 |
| JP | 5-157967 A | 6/1993 |
| JP | 6-148519 A | 5/1994 |
| JP | 7-49459 A | 2/1995 |
| JP | 2006-72098 A | 3/2006 |

* cited by examiner

*Primary Examiner* — Stephen F Husar
*Assistant Examiner* — Meghan Dunwiddie
(74) *Attorney, Agent, or Firm* — Birch, Stewart, Kolasch & Birch, LLP

(57) ABSTRACT

In an endoscope in which light transmitted from an optical fiber bundle using a positive lens is irradiated as illumination light, a glass rod having a diffusion face disposed on one of end faces is arranged between an aperture diaphragm that adjusts an amount of light from a light source and the optical fiber bundle that guides the light from the aperture diaphragm to a distal end portion of the endoscope, and light without a biased angular component is supplied to the optical fiber bundle so as to eliminate illumination light unevenness.

6 Claims, 4 Drawing Sheets

LIGHT WITH BIASED ANGULAR COMPONENT

LIGHT WITH NON-BIASED ANGULAR COMPONENT

ILLUMINATION OPTICAL SYSTEM OF ENDOSCOPE

The disclosure of Japanese Patent Applications No. 2009-278506 on Dec. 8, 2009, including its specification, claims and drawings, is incorporated herein by reference in its entirety.

BACKGROUND OF THE INVENTION

1. Field of the Invention

The present invention relates to a configuration of an illumination optical system of an endoscope or particularly to an illumination optical system that solves uneven illumination light.

2. Description of the Related Art

FIG. 6A shows an illumination optical system of a prior-art endoscope distal end portion described in Japanese Patent Laid-Open No. 5-119272 (Patent Document 1) and Japanese Patent Laid-Open No. 5-157967 (Patent Document 2), and in a distal end portion of an endoscope, an illumination lens including at least one positive lens 2, for example, is arranged on the distal (emitting end) side of a light guide (optical fiber bundle) 1 that leads light from a light source to the distal end portion of the endoscope. This positive lens 2 has at least one face as an aspherical face (h=fθ or h=f sin θ, where h: incident height to lens, θ: emission angle from lens, f: focal distance) and has an advantage that a light-amount loss is small and favorable illuminance distribution can be obtained in a wide angle.

FIG. 6B shows a configuration of the endoscope light-source portion, and light of a light source 3 in the figure has its light amount adjusted by an aperture diaphragm (leaf blade) 4 and is supplied to an incident end of the light guide 1 through a collective lens 5, and the light having passed through the light guide 1 is irradiated to an observed body through the positive lens 2 as the illumination light.

However, in the above-described illumination optical system having the positive lens 2, a phenomenon of unevenness (net-like unevenness) might be caused in the illumination light by uneven density in the optical fiber bundle constituting the light guide 1, and this illumination-light unevenness is particularly remarkable if an angular component of the light incident to the light guide 1 is biased, which is a problem.

That is, as shown in FIG. 6A, since a point $P_1$ and a point $P_2$ are in a conjugation relationship and an emission end of the light guide 1 is located in the vicinity of a conjugated position with an image forming point of the positive lens 2, for example, uneven density of the optical fiber bundle emerges as the illumination light unevenness. Moreover, in a light-source device of an endoscope, as shown in FIG. 6B, a light flux from the light source 3 is taken from one aperture diaphragm (leaf blade) 4, for example, and if a light component La of a light-flux outer periphery is large, light with a biased angular component is supplied to an incident end of the light guide 1, and the above illumination light unevenness is highlighted.

FIG. 7A shows light with a biased angular component and FIG. 7B shows light with a non-biased angular component, and according to the light in FIG. 7B, the illumination light unevenness is not remarkable but if the light with a biased angular component in FIG. 7A is increased, the illumination light unevenness becomes remarkable.

FIGS. 8A and 8B show a configuration of a prior-art illumination optical system with a purpose of solving the above-described illumination-light unevenness, in which FIG. 8A is shown in Japanese Patent Laid-Open No. 6-148519 (Patent Document 3), and Patent Document 3 discloses that a single fiber 7 is inserted between the emission end of the light guide 1 of the endoscope distal-end portion and the positive lens 2 so that the net-like unevenness of the light-guide fiber bundle is hardly shown. FIG. 8B is the one disclosed in Japanese Patent Laid-Open No. 2006-72098 (Patent Document 4), and Patent Document 4 discloses that a sand-blast 8A is worked on a projecting face of the positive lens 8, and a diffusion effect of this sand-blast face reduces uneven light distribution.

However, the configuration in FIG. 8A has nonconformity that the relatively long single fiber 7 is increased in the endoscope distal-end portion, which prolongs the distal end portion and the like, while in the configuration in FIG. 8B, use efficiency of the light supplied to the distal end portion through the light guide 1 is lowered, and even if an aspherical lens with high efficiency is designed for the positive lens 2 or the like, its advantage might be lost. Also, the lowered light use efficiency causes heat generation in the illumination optical system, which leads to the increase of the heat generation at the distal end portion, which is nonconformity. That is, in the endoscope, reduction in a diameter of the distal end portion and increase in pixels of an image pickup element are promoted in view of pain alleviation for a patient and improvement of observation performances, which tends to increase the heat generation in the distal end portion due to the decrease of radiation paths, increase in power consumption of the image pickup element and the like, and from this point of view, too, suppression of the heat generation in the illumination optical system is requested.

On the other hand, as a prior art in which light with a biased angular component is not to be supplied to the light guide, there is one as shown in Japanese Patent Laid-Open No. 7-49459 (Patent Document 5) and Japanese Patent Laid-Open No. 61-177416 (Patent Document 6) in which a light-source optical system is optimized by an exclusive mechanism and an angular component of light incident to the light-guide fiber bundle is controlled. However, such prior arts have a problem that the mechanism for optimization is complicated and expensive.

The present invention was made in view of the above problems and has an object to provide an illumination optical system of an endoscope that can favorably solve unevenness of illumination light with a simple and easy configuration without a need to change the optical system of the endoscope distal-end portion by eliminating incidence of light with a biased angular component to a light guide.

SUMMARY OF THE INVENTION

In order to achieve the above object, the present invention is characterized in that, in an illumination optical light system of an endoscope having an aperture diaphragm that adjusts a light amount from a light source, an optical fiber bundle (light guide) that guides the light from the aperture diaphragm to a distal end portion of the endoscope, and an illumination lens that irradiates the light emitted from the optical fiber bundle to an observed body, a diffusing body is arranged between the aperture diaphragm and the optical fiber bundle.

As the diffusing body, a glass rod or a fiber rod having a diffusion face disposed at least at one end can be arranged.

As the diffusing body, a cover glass having a diffusion face disposed at least at one end can be arranged.

As the diffusing body, a cover glass of a material having a diffusion action (opal, for example) can be arranged.

Another invention is characterized in that, in an illumination optical light system of an endoscope having an aperture diaphragm that adjusts a light amount from a light source, an optical fiber bundle that guides the light from the aperture diaphragm to a distal end portion of the endoscope, and an illumination lens that irradiates the light emitted from the optical fiber bundle to an observed body, an incident end of the optical fiber bundle is formed into a diffusion face.

In the above invention, a positive (power) lens is preferably combined as the illumination lens. Also, the aperture diaphragm can be made in a structure to narrow the light-source light by rotating a single blade around an axis center.

According to the configuration of the present invention, since the light with a biased angular composition as in a case in which the light-source light is narrowed by the aperture diaphragm is converted by the diffusing body or the incident-end diffusion face of the optical fiber bundle to light with a non-biased angular component and the light without a bias in the angular component enters the optical fiber bundle, the illumination light without unevenness can be obtained even if the light is irradiated through the positive lens.

According to the illumination optical system of an endoscope of the present invention, with a simple and easy structure without a need to change the optical system of the endoscope distal-end portion, there is an effect that the light with a biased angular component does not enter the light guide and the illumination-light unevenness can be favorably solved. As a result, there are advantages that the length of the endoscope distal-end portion is not prolonged, increase in the heat generation in the distal end portion is prevented, and there is no need of a mechanism that controls an angular component of incident light.

DESCRIPTION OF THE PREFERRED EMBODIMENTS

First Embodiment

Figure 1:
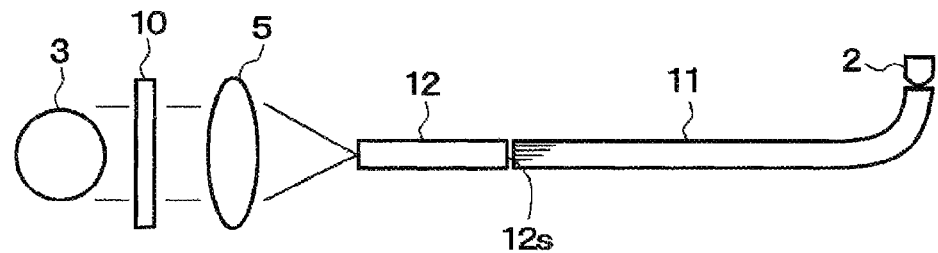
FIG. 1 is a diagram illustrating a configuration of an illumination light optical system of an endoscope according to a first embodiment of the present invention.
Figure 2A:
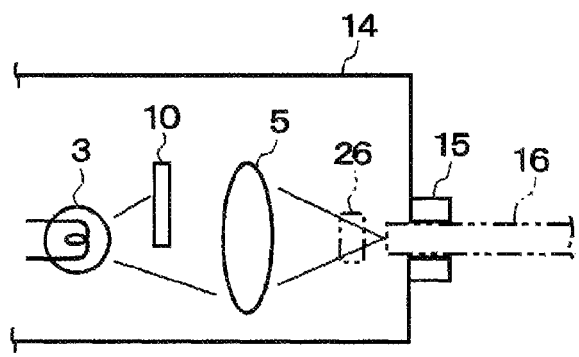
FIG. 2A is a configuration diagram of a light-source device, which is a specific configuration of the illumination optical system of the first embodiment.
Figure 2B:
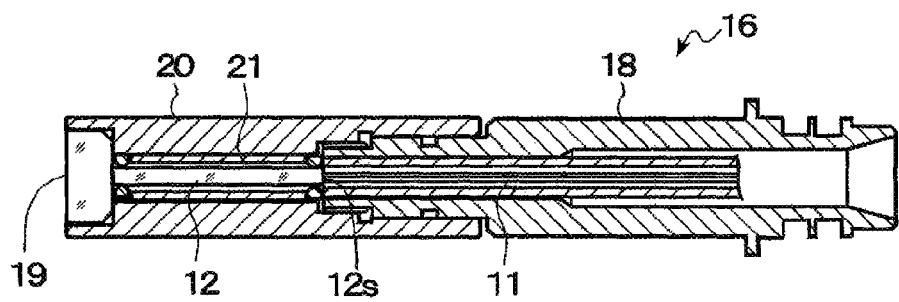
FIG. 2B is a sectional view of a connector portion (light guide incident end portion) on the endoscope side of the first embodiment.
Figure 3:
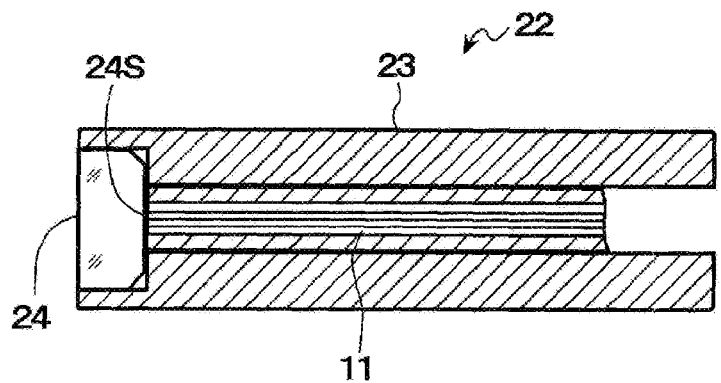
FIG. 3 is a sectional view of an endoscope-side connector portion (light guide incident end portion) of an illumination optical system of a second embodiment.
Figure 5:
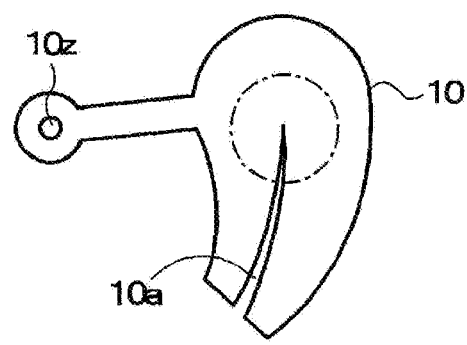
FIG. 5 is a diagram illustrating a configuration of an aperture diaphragm used in the illumination optical system of the embodiment.
Figure 6A:
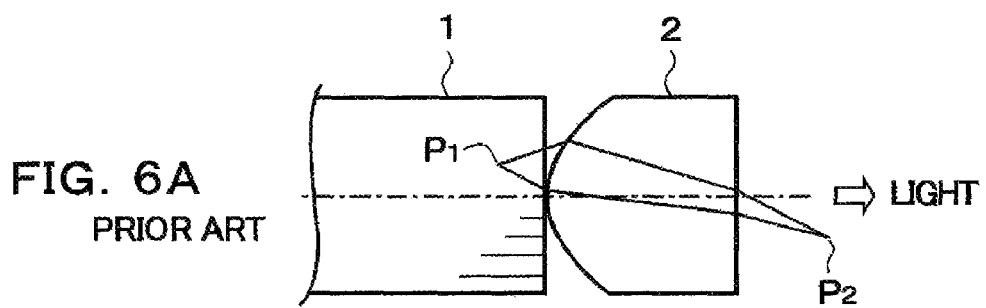
FIG. 6A is a diagram on the endoscope distal-end portion side constituting an illumination optical system of a prior-art endoscope.
Figure 6B:
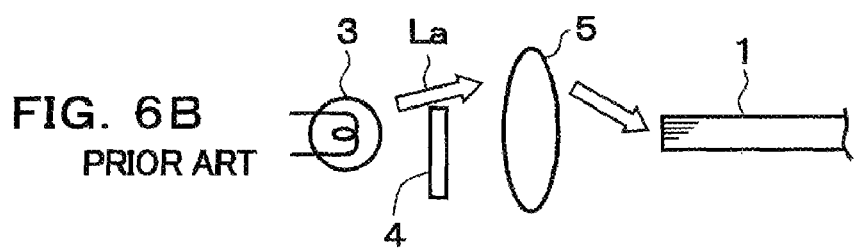
FIG. 6B is a diagram of a light-source device side constituting the illumination optical system of the prior-art endoscope.
Figure 7A:
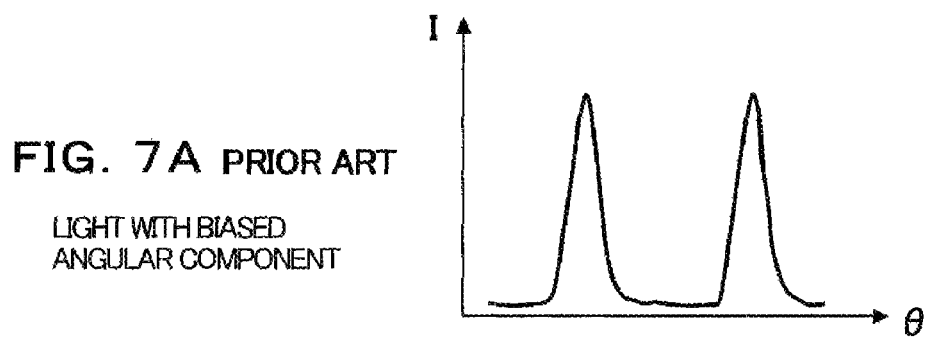
FIG. 7A is a diagram (vertical axis I: intensity, lateral axis θ: angle) illustrating intensity of light with a biased angular component in light incident to the light guide incident end.
Figure 7B:
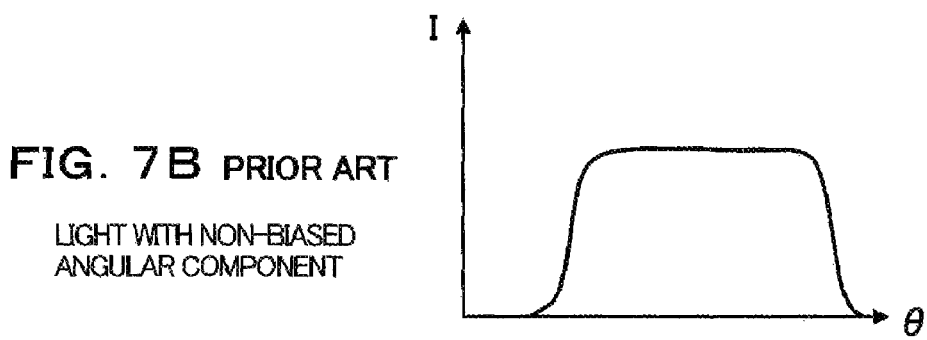
FIG. 7B is a diagram illustrating intensity of light with a non-biased angular component in the light incident to the light guide incident end.
Figure 8A:
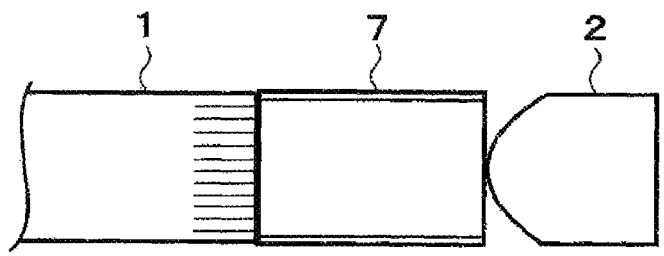
FIG. 8A is a configuration example of the illumination optical system of the prior-art endoscope distal-end portion.
Figure 8B:
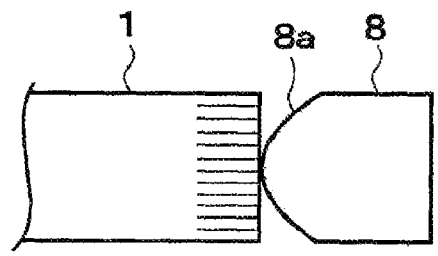
FIG. 8B is another configuration example of the illumination optical system of the prior-art endoscope distal-end portion.

FIGS. 1 to 3 show an illumination optical system of an endoscope according to a first embodiment of the present invention, and in the first embodiment, a single aperture leaf blade 10 is disposed between a light source 3 and a collective lens 5, and at a distal end of an optical fiber bundle 11 (light guide) that guides light of the light source 3 to a distal end portion of the endoscope, at least a positive (power) lens 2 is disposed as an illumination lens. The aperture leaf blade 10 is, as shown in FIG. 5, in the shape (comma-shaped bead) in which a lower end portion of a circular base portion is extended in a state in which a base-portion width is reduced in a direction of rotation around an aperture shaft $10z$, and a notch $10a$ in the shape of a beak whose width is gradually reduced from a distal end of the blade to the center of the circular base portion is disposed.

And as shown in FIG. 1, a glass rod 12 is arranged between the aperture leaf blade 10 (and the collective lens 5) and an incident end of the optical fiber bundle 11 constituting the light guide, and a diffusion face $12s$ on which sand blast is applied to an end face on the optical fiber bundle (incident end) side of this glass rod 12 is formed. This diffusion face $12s$ may be formed on an end face on the collective lens (5) side of the glass rod 12 or may be disposed on both of the end face on the optical fiber bundle side and the end face on the collective lens side.

FIGS. 2A and 2B show a specific configuration of the first embodiment, and the above-described light source 3, the aperture leaf blade 10, and the collective lens 5 are arranged in a light-source device (a processor device may be integrated therewith) 14 of FIG. 2A, and an optical connector 16 of an electronic scope is inserted into and connected with an optical connector receiver 15 of this light-source device 14. And on the optical connector 16 shown in FIG. 2, a cylindrical main body 18 containing the optical fiber bundle (light guide) 11 is disposed, and to a mounting portion of this main body 18, an end member 20 containing the glass rod 12 having the diffusion face $12s$ on one end and a cover glass 19 is screwed and joined. The glass rod 12 of this end member 20 is mounted so that an air layer 21 is formed on the outer periphery thereof, and light incident to this glass rod 12 is totally reflected (multi-reflection) and passes.

The first embodiment is configured as above, and the light from the light source 3 is narrowed by the aperture leaf blade 10 and emitted to the optical connector through the collective lens 5. In this optical connector 16, the light-source light having passed through the cover glass 19 is made to enter the optical fiber bundle 11 through the glass rod 12 and the diffusion face $12s$. In this embodiment, the light-source light narrowed by the aperture leaf blade 10 has increased light with biased spatial intensity distribution as known from the notch $10a$ in FIG. 5, but when it passes through the glass rod 12, the light is transmitted while repeating total reflection by a refraction index difference with the air layer 21 on the outer periphery thereof, and thus, the biased spatial intensity distribution of the light is averaged.

Also, by passing through the diffusion face $12s$, the angle of the light is made more random and by means of both the averaging effect of spatial light intensity distribution by the total reflection of the glass rod 12 and the light angle diffusion effect of the diffusion face $12s$, the bias of the angular component is solved. That is, the light-source light whose light intensity distribution has been averaged can be outputted to the optical fiber bundle 11 at random angles. As a result, in the positive lens 2 in FIG. 1 of the endoscope distal end portion, the illumination light unevenness caused by the presence of the output end of the optical fiber bundle 11 in the vicinity of the conjugation position of the image forming point is solved.

Second Embodiment

FIG. 3 shows a configuration of a second embodiment, and an optical connector 22 of this second embodiment is also inserted into the connector receiver 15 of the light-source device 14 similarly to the first embodiment. In this optical connector 22, the optical fiber bundle 11 and the cover glass 24 are disposed in the cylindrical main body 23, and a diffusion face 24s on which sand blasting is applied to an end face on the optical fiber bundle side (or may be an end face on the optical incidence side on the opposite side) of the cover glass 24, for example, is disposed.

Also, as this cover glass 24, a cover glass of a material having a diffusion action such as opal may be used, for example.

According to such configuration of the second embodiment, even if the angular component of the light-source light through the aperture leaf blade 10 of the light-source device 14 is biased, the angular component is averaged by the diffusion face 24s of the cover glass 24, and light without an angular bias (light with averaged light intensity distribution) is supplied to the optical fiber bundle 11, and as a result, the illumination light unevenness is solved.

In the above-described first and second embodiments, the glass rod 12 and the cover glass 24 as the diffusing body are arranged on the optical connector on the electronic scope side, but an equivalent of the glass rod 12 or an optical member equivalent to the cover glass 24 may be arranged on the light-source device 14 side shown in FIG. 2A or at a position 26 in the vicinity of a collection position of the collective lens 5, for example. Also, in the embodiments, total reflection in the glass rod and the air layer is used, but a fiber rod with a core-clad structure may be used.

Third Embodiment

Figure 4:
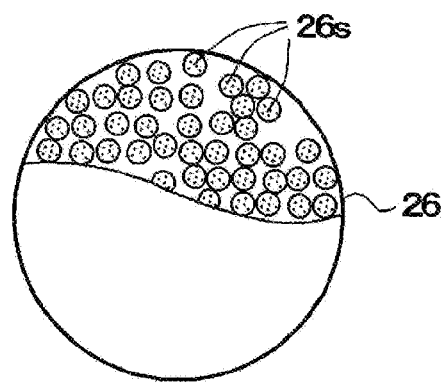
FIG. 4 is a diagram illustrating a configuration of a light guide incident end of an illumination optical system of a third embodiment.

In FIG. 4, a configuration of a third embodiment is shown, and in this third embodiment, in the configuration in FIG. 3 of the second embodiment, the diffusion face 24s is not disposed in the cover glass 24 but in an optical fiber bundle 26 arranged similarly to the optical fiber bundle 11, a diffusion face 26s with the incident end face sand-blasted is disposed. In such third embodiment, too, light without an angular bias is made to enter the optical fiber bundle 26, and the illumination light unevenness is solved.

The diffusion faces 12s, 24s, and 26s may be directly worked on the end face of the glass rod 12, the cover glass 24, and the optical fiber bundle 26 or may be disposed by other methods such as bonding a film-state one or the like.

DESCRIPTION OF SYMBOLS

1 LIGHT GUIDE,
2 POSITIVE LENS
3 LIGHT SOURCE,
10 APERTURE LEAF BLADE
11, 26 OPTICAL FIBER BUNDLE
12 GLASS ROD,
19, 24 COVER GLASS
12s, 24s, 26s DIFFUSION FACE

CITATION LIST

Patent Document 1: JP-A-5-119272
Patent Document 2: JP-A-5-157967
Patent Document 3: JP-A-6-148519
Patent Document 4: JP-A-2006-72098
Patent Document 5: JP-A-7-49459
Patent Document 6: JP-A-61-177416

What is claimed is:

1. An illumination optical system of an endoscope comprising:
    an aperture diaphragm that adjusts an amount of light from a light source;
    an optical fiber bundle that guides the light from the aperture diaphragm to a distal end portion of the endoscope;
    an illumination lens that irradiates the light emitted from the optical fiber bundle to an observed body, wherein the illumination lens comes into contact with the optical fiber bundle, and wherein the illumination lens is a positive aspherical lens; and
    a diffusing body arranged between the aperture diaphragm and the optical fiber bundle, wherein the diffusing body is a glass rod or a fiber rod having a diffusion face disposed at least at one end.

2. The illumination optical system of an endoscope according to claim 1, wherein the diffusing body is a cover glass having a diffusion face formed at least at one end.

3. The illumination optical system of an endoscope according to claim 1, wherein the diffusing body is a cover glass of a material having a diffusion action.

4. The illumination optical system of an endoscope according to claim 1, wherein
    the aperture diaphragm has a structure that narrows the light-source light by rotating a single blade around an axis center.

5. An illumination optical system of an endoscope comprising:
    an aperture diaphragm that adjusts an amount of light from a light source;
    an optical fiber bundle that guides the light from the aperture diaphragm to a distal end portion of the endoscope; and
    an illumination lens that irradiates the light emitted from the optical fiber bundle to an observed body, wherein
    an incident end of the optical fiber bundle is formed into a diffusion face.

6. The illumination optical system of an endoscope according to claim 5, wherein
    the aperture diaphragm has a structure that narrows the light-source light by rotating a single blade around an axis center.

* * * * *